United States Patent
Sawada et al.

(10) Patent No.: US 7,119,218 B2
(45) Date of Patent: Oct. 10, 2006

(54) LOW MELTING POINT TIN SALT OF CARBOXYLIC ACID AND METHOD FOR PRODUCING THE SAME

(75) Inventors: Kouhei Sawada, Hyogo (JP); Kayoko Honda, Hyogo (JP); Hideki Kawamoto, Hyogo (JP); Koji Kada, Osaka (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 10/812,269

(22) Filed: Mar. 29, 2004

(65) Prior Publication Data

US 2004/0192951 A1 Sep. 30, 2004

(30) Foreign Application Priority Data

| Mar. 31, 2003 | (JP) | 2003-096008 |
| Mar. 31, 2003 | (JP) | 2003-096009 |
| Nov. 27, 2003 | (JP) | 2003-397865 |

(51) Int. Cl.
*C07F 7/22* (2006.01)
*C09K 3/00* (2006.01)

(52) U.S. Cl. ............ 556/105; 106/287.19
(58) Field of Classification Search ......... 556/105; 106/287.19
See application file for complete search history.

(56) References Cited

U.S. PATENT DOCUMENTS

| 2,373,387 A | 4/1945 | Elliot |
| 3,162,660 A | 12/1964 | Crayton |
| 5,214,016 A | 5/1993 | Brazdil et al. |

FOREIGN PATENT DOCUMENTS

| EP | 0 235 968 | 9/1987 |
| GB | 1069710 | 5/1967 |
| JP | 55-62400 | 5/1980 |
| JP | 57-63351 | 4/1982 |
| JP | 57-129828 | 8/1982 |
| JP | 60-81704 | 5/1985 |
| JP | 60-157109 | 8/1985 |
| JP | 6-15170 | 5/1993 |
| JP | 6-325637 | 11/1994 |
| JP | 7-186285 | 7/1995 |
| JP | 9-52933 | 2/1997 |
| JP | 10-204332 | 8/1998 |
| JP | 2002-15631 | 1/2002 |
| JP | 2002-175733 | 6/2002 |

OTHER PUBLICATIONS

European Search Report for EP 04 25 1876 dated Jul. 8, 2004.

Derwent Publications Ltd., London, GB; Abstract No. XP002287522 for JP 11 049990, Asahi Glass Co., Ltd., Feb. 23, 1999.

*Primary Examiner*—Porfirio Nazario-Gonzalez
(74) *Attorney, Agent, or Firm*—Amin & Turocy, LLP

(57) ABSTRACT

The present invention provides a low melting point tin salt of aliphatic monocarboxylic acid obtained by a process comprising, reacting an aliphatic monocarboxylic acid having 4 to 30 carbon atoms or its salt and an inorganic tin compound so as to prepare a tin salt of aliphatic monocarboxylic acid, and bringing the tin salt in contact with an oxygen supplying substance.

17 Claims, 2 Drawing Sheets

LOW MELTING POINT TIN SALT OF CARBOXYLIC ACID AND METHOD FOR PRODUCING THE SAME

BACKGROUND OF THE INVENTION

1. Field of the Invention

The present invention relates to a low melting point tin salt of aliphatic monocarboxylic acid that has good solubility in various solvents, a method for producing the same, and a coating liquid containing the tin salt for forming a metal oxide film.

2. Description of the Related Art

Tin salts of aliphatic monocarboxylic acid are used as a catalyst, a material for producing a tin oxide film, a coating material, a stabilizer or the like. When utilizing a tin salt of aliphatic monocarboxylic acid in various applications, the dispersibility of this compound in other materials is important, which is similar to the case of using an aliphatic monocarboxylate comprising a metal other than tin. For example, in order to prepare a resin sheet containing such a tin salt as a stabilizer, a resin, the tin salt and a solvent are mixed together, the mixture is formed into a sheet, and then the solvent is evaporated to form a resin sheet. However, tin salts of aliphatic monocarboxylic acids have a high melting point, and thus, the salt is hardly mixed with the solvent or the resin at ordinary temperature. Therefore, it is difficult to provide the function of the tin salt of aliphatic monocarboxylic acid as a stabilizer uniformly for a long time. Alternatively, when a tin salt of aliphatic monocarboxylic acid is used as a reaction catalyst, the tin salt is hardly mixed with a solvent and other ingredients at ordinary temperature. Therefore, it is difficult to allow the function of the tin salt of aliphatic monocarboxylic acid as a catalyst to be exhibited effectively.

In particular, in recent years, tin salts of aliphatic monocarboxylic acid are utilized as materials for forming tin oxide films that can be used in various fields such as electrodes of electronic devices or optical films. For the production of a tin oxide film by the use of such a tin salt of aliphatic monocarboxylic acid, for example, a method is disclosed in Japanese Laid-Open Patent Publication No. 60-81704, which comprises the process of applying a coating liquid containing a tin carboxylate or a coating liquid containing a tin carboxylate and palladium chloride or chloroplatinic acid onto a substrate to form a film, and baking the same. Japanese Laid-Open Patent Publication No. 60-157109 discloses a method of applying a coating liquid containing a tin carboxylate on a substrate and then performing both irradiation with light having an intensity of 30 mW/cm$^2$ or more and baking so that an oxide tin film is obtained.

In Japanese Laid-Open Patent Publication No. 57-129828, a tin carboxylate is applied onto a surface of a magnetic material and baked so that the magnetic material is coated with a tin oxide film. In Japanese Laid-Open Patent Publication No. 55-62400, a tin carboxylate is applied onto a surface of a substrate and baked so that a tin oxide film is formed on the substrate and this film is used as a transparent filter for X-rays. Moreover, in Japanese Laid-Open Patent Publication No. 60-81704, a solution containing a tin carboxylate and an indium compound is prepared, and this solution is applied onto a surface of a substrate and baked so that an electrode made of an indium-tin oxide (ITO) film is formed on the substrate.

When producing a tin oxide film used as an electrode of an electronic device, an optical film or the like using a tin salt of aliphatic monocarboxylic acid, it is preferable that the tin salt has good solubility in various solvents or solvent mixtures so that a coating liquid containing the tin salt can be applied uniformly on various substrates.

However, in general, the solubility of tin salt of aliphatic monocarboxylic acid, in particular, a tin salt of linear aliphatic monocarboxylic acid in various organic solvents is low. Furthermore, the tin salt can be dissolved in only a limited number of solvents, which makes it difficult to select a solvent having high wettability with respect to a substrate. When using a coating liquid in which such a tin salt of aliphatic monocarboxylic acid is dispersed in a solvent, a uniform coating film cannot be formed when it is applied onto a substrate, and a tin oxide film obtained as a final product by thermal decomposition or other processes becomes non-uniform and opaque. Thus, adequate film characteristics cannot be obtained. The temporal stability of the coating liquid is also poor.

In this way, the tin salt of aliphatic monocarboxylic acid is expected to be used in various applications. But, in general, the tin salt of aliphatic monocarboxylic acid has a high melting point, so that it is difficult to mix the tin salt with a solvent or a resin. Furthermore, the tin salt has poor solubility in various solvents, so that it is difficult to dissolve the tin salt in a desired solvent to use in a desired application, for example, to form a tin oxide film.

SUMMARY OF THE INVENTION

The inventors of the present invention made in-depth research and found that a tin salt of aliphatic monocarboxylate having a low melting point obtained by a specific treatment method can achieve the above-described objects and thus achieved the present invention.

The low melting point tin salt of aliphatic monocarboxylic acid of the present invention is obtained by a process comprising, reacting an aliphatic monocarboxylic acid or its salt and an inorganic tin compound so as to prepare a tin salt of aliphatic monocarboxylic acid; and bringing the tin salt in contact with an oxygen supplying substance.

In a preferred embodiment, the aliphatic monocarboxylic acid has 4 to 30 carbon atoms.

In a preferred embodiment, the aliphatic monocarboxylic acid has 4 to 22 carbon atoms.

In a preferred embodiment, the aliphatic monocarboxylic acid is a linear aliphatic monocarboxylic acid having 4 to 10 carbon atoms.

The method for producing a low melting point tin salt of aliphatic monocarboxylic acid of the present invention comprises: reacting an aliphatic monocarboxylic acid or its salt and an inorganic tin compound so as to prepare a tin salt of aliphatic monocarboxylic acid; and bringing the tin salt in contact with an oxygen supplying substance.

In a preferred embodiment, the oxygen supplying substance is oxygen or a gas containing oxygen.

In a preferred embodiment, the tin salt of aliphatic monocarboxylic acid is brought in contact with the oxygen supplying substance at a temperature that is equal to or higher than the melting point of the tin salt of aliphatic monocarboxylic acid before the contact.

The coating liquid for forming a metal oxide film of the present invention comprises the low melting point tin salt of aliphatic monocarboxylic acid and a solvent.

In a preferred embodiment, the low melting point tin salt is derived from a linear aliphatic monocarboxylic acid having 4 to 10 carbon atoms.

In a preferred embodiment, a 30 wt % ethanol solution of the low melting point tin salt of aliphatic monocarboxylic acid is clear when the solution is allowed to stand at 30° C. for one hour.

In a preferred embodiment, the coating liquid further comprises an indium compound.

In a preferred embodiment, the total amount of the low melting point tin salt of aliphatic monocarboxylic acid and the indium compound is 1 to 95 wt % in the coating liquid.

In a preferred embodiment, the solvent is at least one selected from the group consisting of hydrocarbon solvents, alcohol solvents, ester solvents, ether solvents, and ketone solvents.

Therefore, the invention described herein makes possible the objectives of, providing a low melting point tin salt of aliphatic monocarboxylic acid that can be used as various catalysts, stabilizers, film materials or the like in a wide range of fields; providing a low melting point tin salt of aliphatic monocarboxylic acid that is derived from a linear aliphatic monocarboxylic acid having 4 to 10 carbon atoms, that is liquid at 30° C., that is soluble in various solvents, and that can be used preferably in a coating liquid for forming a tin oxide film; providing a method for producing the low melting point tin salt of aliphatic monocarboxylic acid; providing a coating liquid for forming a metal oxide film, wherein the coating liquid contains the tin carboxylate, wherein the metal oxide film has high transparency, has a sufficient thickness and area, and is smooth and has stable characteristics; providing a coating liquid that can form a tin oxide film that has the above-described excellent features, and can be used in various fields such as electrodes of electronic devices, optical films, display devices or the like; and providing a coating liquid that contains an indium compound in addition to the low melting point tin salt of aliphatic monocarboxylic acid, and can form an indium-tin oxide film that is smooth and transparent and has excellent conductivity without causing cracks.

DESCRIPTION OF THE PREFERRED EMBODIMENT

Figure 1:
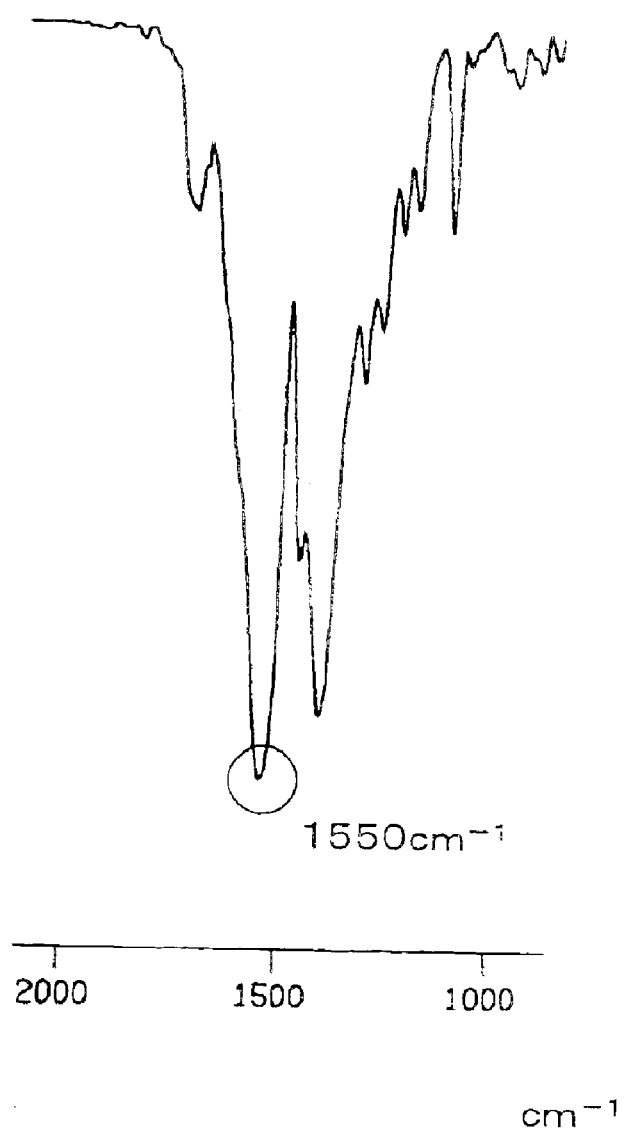
FIG. 1 is a chart showing an infrared absorption spectrum of tin caproate (before an oxygen contact treatment) obtained in Preparation Example 1.1.

The low melting point tin salt of aliphatic monocarboxylic acid of the present invention can be obtained by reacting an aliphatic monocarboxylic acid or its salt and an inorganic tin compound so as to prepare a tin salt of aliphatic monocarboxylic acid, and bringing the same in contact with an oxygen supplying substance. In the specification of the present invention, "oxygen supplying substance" refers to oxygen or a substance that can supply oxygen.

Hereinafter, a material for producing the low melting point tin salt of aliphatic monocarboxylic acid, a method for producing the tin salt and a coating liquid containing the tin salt will be described in that order.

1. Materials for Preparing a Tin Salt of Aliphatic Monocarboxylic Acid (starting material)

The aliphatic monocarboxylic acid for preparing a tin salt of aliphatic monocarboxylic acid (i.e., starting material) used to produce the low melting point tin salt of aliphatic monocarboxylic acid of the present invention preferably has 4 to 30 carbon atoms. This aliphatic monocarboxylic acid may be either a saturated fatty acid or an unsaturated fatty acid. Preferable examples of the fatty acid include n-butyric acid, isobutyric acid, butenoic acid, valeric acid, isovaleric acid, n-caproic acid, hexenoic acid, 2-ethylbutyric acid, enanthic acid (n-heptanoic acid), caprylic acid (n-octanoic acid), octenoic acid, 2-ethylhexanoic acid, pelargonic acid (n-nonanoic acid), capric acid (n-decanoic acid), decenoic acid, lauric acid, a myristic acid, myristoleic acid, palmitic acid, isopalmitic acid, palmitoleic acid, stearic acid, lignoceric acid, cerotic acid, montanoic acid, isostearic acid, oleic acid, arachic acid, ricinoleic acid, linoleic acid, behenic acid, and erucic acid. Mixed fatty acids derived from animal or vegetable oils or fats can be also employed such as beef tallow fatty acid, soybean oil fatty acid, coconut oil fatty acid, and palm oil fatty acid. Examples of salts of the above-mentioned aliphatic monocarboxylic acids include alkali metal salts such as sodium salts and potassium salts; ammonium salts; and organic amine salts such as monoethanolamine salts, diethanolamine salts, and monopropanolamine salts. These aliphatic carboxylic acids or their salts can be employed alone or in combination of two or more.

When the number of carbon atoms of the aliphatic monocarboxylic acid is less than 4 or more than 30, a tin salt of the monocarboxylic acid having a sufficiently low melting point may not be obtained from the process of reacting the carboxylic acid with a tin compound, followed by an oxygen contact treatment. For example, a tin salt having a melting point 20° C. or more lower than that before the contact treatment may not be obtained. When such a tin salt of the monocarboxylic acid is mixed with a solvent or a resin at relatively low temperature, the tin salt may not be dissolved or dispersed in the solvent or the resin. Therefore, the resultant resin may become opaque, or effects of the tin salt such as a catalytic effect or a stabilizing effect may not be obtained sufficiently and uniformly.

The above-mentioned aliphatic monocarboxylic acid preferably has 4 to 22 carbon atoms. When an aliphatic monocarboxylic acid having such a carbon number is employed, the resultant low melting point tin salt has a melting point that is at least 25° C. lower than that of the tin salt before the contact with the oxygen supplying substance described later.

When a linear aliphatic monocarboxylic acid having 4 to 10 carbon atoms, preferably 4 to 7 carbon atoms or its salt is employed, a low melting point tin salt of aliphatic monocarboxylic acid having a sufficiently low melting point can be obtained. Such a low melting point tin salt is excellently soluble in various solvents. Furthermore, such a tin salt is liquid at 30° C. Examples of the above aliphatic monocarboxylic acid include n-butyric acid, valeric acid, n-caproic acid, enanthic acid, caprylic acid, pelargonic acid, and capric acid. Examples of their salts include alkali metal salts, ammonium salts and organic amine salts as described above.

There is no limitation regarding the inorganic tin compound used in the production of the low melting point tin salt of aliphatic monocarboxylic acid of the present invention, as long as it is water-soluble and can react with the above-described aliphatic monocarboxylic acid or its salt. For example, stannous compounds such as stannous oxide, stannous chloride, stannous hydroxide, stannous sulfate, and stannous nitrate and stannic compounds such as stannic chloride can be used. Among these, stannous compounds, in particular, stannous chloride, which is soluble in water stably and can react efficiently with a carboxylic acid salt, are preferable.

The oxygen supplying substance used in the present invention is oxygen or a substance that can supply oxygen as mentioned above. Examples of substances that can supply oxygen include ozone and peroxides, and examples of peroxides include hydrogen peroxide.

2. Tin Salt of Aliphatic Monocarboxylic Acid (starting material)

A tin salt of aliphatic monocarboxylic acid can be obtained by reacting the aliphatic monocarboxylic acid or its salt with the inorganic tin compound. As the reaction method, a double decomposition method, a direct method or other methods used in the art can be employed. In the double decomposition method, a water-soluble salt (e.g., alkali salt, ammonium salt, organic amine salt, or the like) of the aliphatic monocarboxylic acid and a water-soluble inorganic tin compound are separately dissolved in an aqueous solvent such as water, and the resultant solutions are mixed. Then, a salt exchange reaction occurs, so that a tin carboxylate is formed. In the direct method, the aliphatic monocarboxylic acid and the inorganic tin compound (e.g., stannous oxide or stannous hydroxide) are directly mixed at a temperature of 100 to 200° C. so as to effect a reaction, and thus a tin carboxylate is formed.

Of these methods, in particular, it is preferable to employ the double decomposition method. When this method is employed, a tin salt of aliphatic monocarboxylic acid can be produced stably at a lower temperature than in the direct method. Therefore, decomposition products tend not to be formed, so that it is not necessary to filter the decomposition products. Furthermore, the characteristics of a low melting point tin salt of aliphatic monocarboxylic acid obtained by a contact with an oxygen supplying substance described later are good, and the temporal stability thereof is also high.

The method for producing a tin salt of aliphatic monocarboxylic acid by the double decomposition method will be described below. In order to produce a tin salt of aliphatic monocarboxylic acid by this method, for example, first the aliphatic monocarboxylic acid is dissolved in an aqueous solvent such as water. Herein, "aqueous solvent" refers to water or a solvent containing water as the main component. For example, water containing alcohol can be used. In order to dissolve the aliphatic monocarboxylic acid in an aqueous solvent, a water-soluble salt (e.g., a salt of alkali metal such as sodium or potassium, a salt of ammonium or organic amine, or the like) of the aliphatic monocarboxylic acid is used. Alternatively, the aliphatic monocarboxylic acid is dissolved directly in an aqueous solvent solution containing alkali such as a sodium hydroxide aqueous solution, a calcium hydroxide aqueous solution or aqueous ammonia, resulting in a tin salt of aliphatic monocarboxylic acid that is in a dissociated state in the aqueous solvent. When using an aliphatic monocarboxylic acid having a comparatively large number of carbon atoms such as 14 or more, it is preferable to employ a potassium salt of the carboxylic acid that has high solubility in water or to form a potassium salt dissociated in a solvent. By using such a highly water-soluble salt, a reaction can be carried out at an even lower temperature and a tin monocarboxylate having high purity can be obtained.

Separately, the inorganic tin compound is dissolved in an aqueous solvent. Then, a solution containing the water-soluble salt of the aliphatic monocarboxylic acid and a solution containing the inorganic tin compound are mixed, so that a salt exchange reaction proceeds, and thus a tin salt of aliphatic monocarboxylic acid is formed.

In the above reaction, the salt of aliphatic monocarboxylic acid is used in an excess molar amount compared with the amount of the inorganic tin compound. Preferably, the salt of aliphatic monocarboxylic acid is used in 2 to 5 moles, more preferably 2 to 3 moles with respect to one mole of the inorganic tin compound. In particular, a ratio of more than 2 to about 2.1 moles (e.g., 2.05 to 2.10 moles) is preferable. When the amount of the aliphatic monocarboxylic acid salt is less than 2.0 moles, a decomposition product derived from unreacted inorganic tin compounds is produced, and it is necessary to separate the decomposition product by filtration or the like. When the amount of the salt of aliphatic monocarboxylic acid exceeds 2 moles (about 2.4 moles as the practical amount provided for reaction), the amount of the produced tin salt of aliphatic monocarboxylic acid is not increased, so that the productivity is reduced. Furthermore, more washing is required in order to remove excessive carboxylic acid salt contained in the system, so that the formed tin salt of aliphatic monocarboxylic acid may decompose during the washing. In the case where a decomposition product occurs, filtration or the like is necessary.

The reaction temperature in the double decomposition method is preferably 60° C. or less. When a reaction is carried out at a temperature of more than 60° C., the inorganic tin compound may decompose so that dark green stannous oxide may be formed, and the reaction may not proceed.

Thus, by the double decomposition method, a tin salt of aliphatic monocarboxylic acid is produced in an aqueous solvent. This tin salt is generally washed with water, and then dehydrated, and dried. It is particularly preferable to perform the above-mentioned processes at a temperature of 60° C. or less until the washing process, which is similar to the temperature in the above-mentioned reaction process. This is because the produced tin salt may decompose due to impurities such as by-products. When an alkali metal salt, amine salt, or ammonia salt of aliphatic monocarboxylic acid is used as a raw material, an alkali metal salt, amine salt, or ammonia salt produced in the system by the reaction and the excessive carboxylic acid salt can be easily removed by the washing with water, so that a tin salt of aliphatic monocarboxylic acid having high purity can be obtained.

3. Low Melting Point Tin Salt of Aliphatic Monocarboxylic Acid

A low melting point tin salt of aliphatic monocarboxylic acid can be obtained by bringing the tin salt of aliphatic monocarboxylic acid in contact with (i.e., obtained by allowing the tin salt of aliphatic monocarboxylic acid to come into contact with) an oxygen supplying substance. In this specification, bringing in contact with an oxygen supplying substance may be expressed as "performing an oxygen contact treatment" or "performing a contact treatment". "Oxygen supplying substance" refers to oxygen or a substance that can supply oxygen, as described above. Examples thereof include oxygen gas and gases containing oxygen such as air, active oxygen compounds such as ozone, and peroxides such as hydrogen peroxide. Examples of methods for the contact with an oxygen supplying substance include a method that employs a gaseous substance such as oxygen, a gas containing oxygen or ozone as the oxygen supplying substance and the tin salt of aliphatic monocarboxylic acid is allowed to stand in an atmosphere of such a gaseous substance; a method of bubbling the gaseous oxygen supplying substance in a melted tin salt of aliphatic monocarboxylic acid; and a method of mixing the tin salt of aliphatic monocarboxylic acid with a liquid oxygen supplying substance such as a hydrogen peroxide solution.

Of the above-described methods, it is preferable to perform an oxygen contact treatment of the tin salt of aliphatic monocarboxylic acid using oxygen gas or a gas containing oxygen, and it is particularly preferable to use oxygen gas having a purity of at least 50%. When taking the time required for the oxygen contact treatment into consideration, it is most preferable to use oxygen gas. Since the wider the contact area of the oxygen supplying substance and the tin salt of aliphatic monocarboxylic acid is, the larger the efficiency is. More specifically, it is preferable to heat the tin salt of aliphatic monocarboxylic acid to a temperature of its melting point or higher for melting, and then bubble oxygen gas or the like in the molten tin salt. Since ozone causes a high burden on the environment, countermeasures for the environmental burden are necessary. When using an oxygen supplying substance comprising peroxide such as a hydrogen peroxide solution, the formed tin salt of aliphatic monocarboxylic acid tends to decompose, so that it is preferable to remove excessive peroxide rapidly after the treatment.

The melting point of the resultant tin salt of aliphatic monocarboxylic acid (i.e., a low melting point tin salt of aliphatic monocarboxylic acid) obtained by performing a treatment in this manner is lower than that of the tin salt of aliphatic monocarboxylic acid before the treatment (i.e., starting material). The melting point tends to be at least 20° C. lower than the tin salt of carboxylic acid before the treatment. Generally, when an aliphatic monocarboxylic acid having 4 to 22 carbon atoms is employed, the resultant low melting point tin salt has a melting point that is at least 25° C. lower than that of the tin salt before the contact with the oxygen supplying substance. Furthermore, a low melting point tin salt of linear aliphatic monocarboxylic acid having 4 to 10 carbon atoms is liquid at 30° C. Generally, the above-mentioned tin salt of carboxylic acid with such a lowered melting point has increased solubility in various solvents compared with a tin salt before the oxygen contact treatment.

The weight of the obtained low melting point tin salt of aliphatic monocarboxylic acid is increased compared with that of the original tin salt of aliphatic monocarboxylic acid. The weight increased by the oxygen contact treatment is not reduced by degasification or vacuum drying, and thus, the phenomenon in which the weight is increased by the oxygen contact treatment is irreversible. It is preferable that the weight of the low melting point tin salt of aliphatic monocarboxylic acid is increased at a ratio of more than 1 wt % on the basis of the weight of a tin atom compared with the weight of the tin salt before oxygen contact, and it is more preferable that the weight is increased at a ratio of more than 10 wt %. Such a low melting point tin salt of aliphatic monocarboxylic acid has a melting point of at least 20° C. lower than that of the original tin salt, and in particular, in the case of the low melting point tin salt of linear aliphatic monocarboxylic acid having 4 to 10 carbon atoms is liquid at 30° C. When the weight increase ratio is 1 wt % or less, the melting point may not be reduced by 20° C. or more, and in the case of the low melting point tin salt of linear aliphatic monocarboxylic acid having 4 to 10 carbon atoms may not be liquid at 30° C. The tin content of the tin salt of aliphatic monocarboxylic acid can be measured using a known analysis method such as thermogravimetry.

The thus obtained low melting point tin salt of aliphatic monocarboxylic acid can be identified by a known analysis method such as infrared absorption spectroscopy or nuclear magnetic resonance spectroscopy. According to the infrared absorption spectrum, the tin salt of aliphatic monocarboxylic acid before the treatment exhibits a strong peak derived from a C=O double bond in the vicinity of 1550 cm$^{-1}$, whereas the low melting point tin salt of aliphatic monocarboxylic acid after the oxygen contact treatment exhibits a strong peak derived from a C=O double bond in the vicinity of 1610 cm$^{-1}$.

The low melting point tin salt of aliphatic monocarboxylic acid can be obtained easily by the above-described method. Such a tin salt can be used as various catalysts, stabilizers, materials for forming films or the like in a wide range of fields. In particular, it can be used preferably as a material for forming a metal oxide film, as described below.

4. Materials Contained in Coating Liquid for Forming Metal Oxide Film

The coating liquid for forming a metal oxide film of the present invention contains the low melting point tin salt of aliphatic monocarboxylic acid, and a solvent and, if necessary, a metal compound containing a metal other than tin, and various additives.

4.1 Low Melting Point Tin Salt of Aliphatic Monocarboxylic Acid Contained in Coating Liquid The coating liquid for forming a metal oxide film of the present invention contains the low melting point tin salt of aliphatic monocarboxylic acid. The aliphatic monocarboxylic acid that is a raw material of this low melting point tin salt of aliphatic monocarboxylic acid preferably has 4 to 10 carbon atoms, and more preferably is a linear monocarboxylic acid having 4 to 7 carbon atoms that is liquid at 30° C. When such an aliphatic monocarboxylic acid is employed, the resultant low melting point tin salt of aliphatic monocarboxylic acid has an excellent solubility in solvents. When the obtained low melting point tin salt of aliphatic monocarboxylic acid is made into a 30wt % solution of ethanol and the solution is allowed to stand at 30° C. for one hour, then the solution is clear and opaqueness does not occur. When such a low melting point tin salt of aliphatic monocarboxylic acid is used as a material for forming a tin oxide film, a transparent coating liquid can be obtained, and the oxide tin film obtained as a final product is transparent and has a sufficient strength. Especially, a low melting point tin salt of linear aliphatic monocarboxylic acid having 4 to 10 carbon atoms has an excellent solubility in various solvents. Thus, when a coating film formed from a coating liquid containing such a tin salt is baked, the shrinkage is smaller than that of a film formed from a coating liquid containing a tin monocarboxylate having a branched chain. Therefore, cracks hardly occur and a good film can be obtained. In particular, such a carboxylic acid salt is preferable, because cracks hardly occur during baking, and a tin oxide film having uniform film characteristics can be obtained even when preparing a thick tin oxide film having a large area.

The low melting point tin salt of aliphatic monocarboxylic acid of the present invention has good solubility in various organic solvents. Therefore, for example, when preparing an oxide film (e.g., indium-tin oxide (ITO) film) containing tin and other metals, using a coating liquid containing the tin salt and other metal compounds, a solvent can be selected from a very wide range of solvents, so that a suitable solvent can be selected in accordance with the metal compound that is to be employed. The obtained coating liquid can provide a film having adequate characteristics when it is applied on a substrate of glass or resin, and the resultant coating film is dried and baked.

4.2 Solvent

Since the low melting point tin salt of aliphatic monocarboxylic acid of the present invention is soluble in various solvents at a high concentration, there is no limitation regarding the solvent to be used for the coating liquid. For example, the following solvent can be employed: an alcohol solvent such as ethanol; an aromatic hydrocarbon solvent such as toluene; an aliphatic hydrocarbon solvent such as hexane; a halogen-containing solvent such as chloroform; a ketone solvent such as acetone and acetylacetone; an ether solvent such as diethyl ether; an amide solvent such as dimethylformamide; an ester solvent such as ethyl acetate; and a carboxylic acid solvent such as acetic acid. These solvents may be used alone or in combination. The carboxylic acid solvents may be a mixed solvent with water. An example thereof is an acetic acid aqueous solution. Among these, a solvent that contains neither a halogen nor nitrogen is preferable. This is because when a film is formed from a coating liquid that employs a solvent containing these elements, the obtained tin oxide film contains a halogen compound or a nitride, so that the film characteristics may be impaired. In particular, in the case of a coating liquid for producing an ITO film, as described later, it is preferable to select a solvent that contains neither a halogen nor nitrogen in order to ensure the film characteristics such as transparency and conductivity. Examples of such a solvent include hydrocarbon solvents, alcohol solvents, ester solvents, ether solvents and ketone solvents. Among these, it is preferable to use an alcohol solvent having a high polarity such as ethanol in terms of the wettability to a substrate or the environmental burden. In particular, in the case of coating a glass substrate, it is preferable to use an ester solvent such as propylene glycol monomethyl ether acetate, which has a high affinity with glass together with an alcohol solvent.

When the coating liquid of the present invention contains a metal compound other than the low melting point tin salt of aliphatic monocarboxylic acid, a solvent is selected, taking the solubility of the compound into consideration, as described above. For example, when the coating liquid of the present invention is used for producing an ITO film containing an indium compound, wherein the coating liquid contains an indium salt of monocarboxylic acid having 5 to 8 carbon atoms (which is preferably used; refer to the description below), then a hydrocarbon solvent or a mixed solvent of a hydrocarbon solvent and an alcohol solvent can be used preferably. Examples of the hydrocarbon solvent include hexane and toluene, and examples of the alcohol solvent include methanol, ethanol, n-propanol, and isopropanol. A highly transparent and smooth film can be formed by using the coating liquid containing such solvents.

4.3 Metal Compound Containing Metal other than Tin

As the metal compound containing metal other than tin that can be contained in the coating liquid described above, various compounds are suitable such as a compound containing the following metal component (e.g., a salt of an organic acid containing the following metal): a metal of Group II such as magnesium, calcium, strontium and barium; a metal of Group III such as yttrium, and a metal of the lanthanide series such as lanthanum, cerium, praseodymium, neodymium, samarium, europium, gadolinium, terbium, dysprosium and holmium; a metal of Group IV such as titanium and zirconium; a metal of Group V such as vanadium and niobium; a metal of Group VI such as chromium; a metal of Group VII such as manganese; a metal of Group VIII such as iron; a metal of Group IX such as cobalt; a metal of Group X such as nickel; a metal of Group XI such as copper, silver and gold; a metal of Group XII such as zinc; a metal of Group XIII such as boron, aluminum, gallium and indium; a metal of Group XIV such as silicon and germanium; and a metal of Group XV such as antimony and bismuth. Examples of compounds containing such a metal include cobalt acetate, zinc acetate, silicon tetraacetate, magnesium caproate, and indium caproate.

When preparing a coating liquid for forming a tin oxide film, these compounds can be contained in a range that does not impair the effect of the present invention. When it is also desired to obtain the characteristics derived from a metal other than tin, the kind and the amount of the metal salt are determined as appropriate, depending on the purpose.

For example, when preparing a coating liquid for providing an ITO film, the coating liquid contains an indium compound, in addition to the low melting point tin salt of aliphatic monocarboxylic acid. The indium compound that can be contained in the coating liquid for providing an ITO film will be described below.

The indium compound that can be contained in the coating liquid for providing an ITO film of the present invention can be any compound, as long as it is soluble in a solvent and can be converted into indium oxide by being baked. Examples thereof include indium carboxylate, indium chloride, indium iodide, indium nitrate, indium sulfate, acetylacetone indium salt, indium alkoxide, indium sulfamate, and indium tris-benzoyl methanate. Among these compounds, indium compounds that can form a hydrate such as indium chloride and indium nitrate can be used in the form of a hydrate. The above-described indium compounds can be used alone or in combination.

Among the above-described indium compounds, indium chloride, indium nitrate, acetylacetone indium salt and indium carboxylate having 1 to 8 carbon atoms have good solubility in solvents and are preferable as indium compounds for forming an ITO film.

Among the preferable compounds as indium compounds for forming an ITO film, indium chloride has particularly high solubility in various solvents. For example, it can be dissolved satisfactorily in alcohol solvents such as ethanol and butanol, ether solvents such as THF, ketone solvents such as acetylacetone, ethyl acetoacetate, and methyl acetoacetate. Therefore, a coating liquid can be prepared easily to form an ITO film. However, indium chloride is highly volatile, so that when a coating film is formed using a coating liquid containing indium chloride and baking is performed, the indium chloride is evaporated so that the resultant ITO film may be opaque. Furthermore, since this compound contains chlorine, harmful chlorine gas may be formed during baking. Therefore, it is necessary to limit the film formation conditions or install an apparatus for trapping chlorine gas or a purifying apparatus.

Indium nitrate is soluble in ketone solvents, a typical example of which is acetylacetone, and is also soluble in a mixed solvent of a hydrocarbon solvent and a ketone solvent. Acetylacetone indium salt is satisfactorily soluble in hydrocarbon solvents such as toluene, and ketone solvents such as acetone and acetylacetone. Indium nitrate and acetylacetone indium salt are preferable in that they are free from halogen such as chlorine, so that no harmful gas is produced during baking. However, when a film is formed using the coating liquid containing any of these compounds, aggregation may occur during pre-baling or baking.

With respect to the indium carboxylate mentioned above, the number of carbon atoms of this compound is preferably 1 to 8. Indium carboxylate having 9 or more carbon atoms has low solubility in a solvent so that it is difficult to prepare a coating liquid containing the same.

Among the indium carboxylate having 1 to 8 carbon atoms, an indium carboxylate having 1 to 4 carbon atoms is soluble in a ketone solvent and also soluble in a mixed solvent of a hydrocarbon solvent and a ketone solvent. However, as in the case of the indium nitrate, aggregation may occur during pre-baking an d baking, so that care is necessary for handling. Among the indium carboxylate having 1 to 8 carbon atoms, an indium carboxylate having 5 to 8 carbon atoms is more preferable. The indium carboxylate having 5 to 8 carbon atoms is soluble in a ketone solvent, a hydrocarbon solvent, a mixed solvent of a hydrocarbon solvent and a ketone solvent, an ether solvent, a mixed solvent of a hydrocarbon solvent and an alcohol solvent. The indium carboxylate having 5 to 8 carbon atoms is soluble in various solvents such as a hydrocarbon solvent. Thus, when a coating liquid containing such a compound is employed, aggregation and non-uniformity hardly occurs, and furthermore, harmful gas does not generate during baking of the resultant coating film. As a result, the ITO film finally obtained is smooth and has almost no cracks.

Among the indium carboxylate having 5 to 8 carbon atoms, salts of monocarboxylic acid are easily handled, because they have a low viscosity when dissolved in a solvent. Polycarboxylic acid indium salts such as dicarboxylic acid salts or tricarboxylic acid salts have a very high viscosity when dissolved in a solvent. Therefore, the obtained coating liquid has a high viscosity, so that the obtained film tends not to be uniform, and therefore care is necessary for handling.

As described above, the tin compound contained in a coating liquid of the present invention is preferably a liquid tin salt of linear aliphatic monocarboxylic acid. In this case, in the indium monocarboxylate having 5 to 8 carbon atoms as described above, it is more preferable that monocarboxylic acid constituting the indium monocarboxylate has a linear alkyl group. In this way, when the tin salt of carboxylic acid in which the alkyl group is linear, it is preferable to employ an indium carboxylate in which the alkyl group is liner. In the coating liquid, the affinity between the alkyl groups of these compounds is strong, so that when the coating liquid is applied onto a substrate, a strong and stable coating film having a very high film density can be formed. When such a coating film is baked, the resultant ITO film has no cracks and has excellent transparency.

When an ITO film is prepared using a coating liquid containing an indium salt of linear monocarboxylic acid having 5 to 8 carbon atoms and a tin salt of linear aliphatic monocarboxylic acid that is liquid, an ITO film having almost no cracks and excellent transparency and smoothness can be formed.

4.4 Other Materials that can be Contained in the Coating Liquid

The coating liquid of the present invention contains additives, if necessary.

Examples of the additives that can be contained in the coating liquid of the present invention include a thickener, an antifoamer, a leveling agent, and a viscosity modifier. Examples of the thickener include ethyl cellulose and nitrocellulose. Examples of the antifoamer and leveling agent include anionic surfactants, nonionic surfactants, cationic surfactants, and polymer leveling agents. The viscosity modifier may be contained for the purpose of modifying the viscosity during baking, and in general, organic acid magnesium salt having at least 11 carbon atoms is used for this. Examples of such a compound include magnesium undecanoate, magnesium dodecanoate, magnesium tridecanoate, magnesium tetradecanoate, magnesium heptadecanoate, and magnesium octadecanoate. These additives can be contained in a range that does not impair the effect of the present invention, that is, in a range in which all of the components can be dissolved uniformly in a solvent.

5. Preparation of Coating Liquid for Forming Metal Oxide Film and Preparation of Metal Oxide Film using the Coating Liquid Specifically, the coating liquid for forming a metal oxide film of the present invention can be obtained by dissolving the liquid tin salt of aliphatic monocarboxylic acid, and if necessary, a metal compound containing a metal other than tin, and various additives in a solvent. Each components are mixed by an ordinary method.

In the coating liquid, it is preferable that the low melting point tin salt of aliphatic monocarboxylic acid is contained in a ratio of 1 wt % to 95 wt %, more preferably 5 to 95 wt %, and particularly preferably 5 to 50 wt %, on the basis of the weight of the entire coating liquid. When a metal compound containing a metal other than tin is contained, the amount of the metal compound is determined as appropriate, depending on the properties of a desired film. For example, when forming an ITO film on a substrate, in general, the compounds are contained such that indium atoms are contained in a ratio of 5 to 10000 moles, preferably 10 to 10000 moles, per 1 mol of the tin atom contained in the coating liquid. In order to obtain an ITO film having particularly good conductivity, indium atoms are preferably contained at a ratio of 10 to 10000 moles per 1 mol of the tin atom. When a metal compound containing a metal other than tin is contained, it is preferable that the total amount of this compound and the low melting point tin salt of aliphatic monocarboxylic acid falls into the above mentioned range i.e., 1 wt % to 95 wt %). When the total amount of these components is less than 1 wt %, the solid content is low, so that the thickness of the obtained film is too small for practical use, or it is necessary to repeat an operation of coating and then baking many times, which may deteriorate the productivity. When the amount exceeds 95 wt %, dissolution in a solvent becomes difficult, so that non-uniformity tends to occur during application of the coating liquid. The content can be determined as appropriate, taking into consideration the type of a substrate on which a tin oxide film or a metal oxide film containing tin is to be formed, the coating method, the desired thickness of the film or the like. For example, when coating a glass substrate by spin coating, as described later, a coating liquid having any concentration from 5 wt % to 95 wt % can provide a tin oxide film. However, when the concentration is comparatively high, it may be necessary to increase the rotation speed of spin coating or other improvements may be necessary.

In order to prepare a metal oxide film using this coating liquid, first the coating liquid is applied (coated) onto a desired substrate. Then, a metal oxide film is obtained generally employed methods for forming an oxide film, such as baking the obtained coating film or performing irradiation with ultraviolet rays.

As a substrate used for the preparation of the film, any substrate generally known in the art can be used. For example, glass substrates or a substrate made of a resin such as polycarbonate or epoxy resin can be used. In particular, when forming a metal oxide film by baking at 200° C. or more, glass is preferable. When forming a film by irradiation with ultraviolet rays, it is preferable to use a resin substrate such as a resin plate, sheet, or film.

As a method for coating a substrate with the coating liquid, coating with a brush, immersion, spinning, spraying, screen printing, roll coating, pattern formation by inkjet or any other methods used in the art can be employed. In general, a substrate on which a coating film is formed is subjected to pre-baking in order to evaporate the solvent and to dry the coating film, and then is subjected to baking. When performing baking, the temperature of the baking is 200° C. or more. When a tin salt of unsaturated aliphatic monocarboxylic acid is contained in the coating liquid and the baling temperature is too low, the film may be colored.

Therefore, for example, care is necessary to perform baking at a higher temperature (e.g., 300° C. or more) over a longer time than when a coating liquid containing a tin salt of saturated aliphatic monocarboxylic acid is used.

In the preparation of the metal oxide film, the coating liquid has good affinity with various substrates such as glass substrates or resin substrates, and can be applied uniformly onto such a substrate in any thickness. When the tin carboxylate is linear, in particular, there are few voids between the molecules, and therefore shrinkage of the coating film tends not to occur during baking of the film. Therefore, when forming a thick tin oxide film in a large area, cracks hardly occur, and the film characteristics become uniform. When a film is prepared using the coating liquid for producing an ITO film containing an indium compound, a smooth and transparent ITO film having excellent conductivity can be formed without causing cracks. Such an ITO film can be used for transparent electrodes of plasma display panels, liquid crystal display panels, touch panels, or solar batteries, or can be used as an electromagnetic shielding material, an infrared reflection film for automobiles or architectural window or the like.

EXAMPLES

The present invention will be described more specifically by way of examples that include a method for producing the low melting point tin salt of aliphatic monocarboxylic acid, but the present invention is not limited by these examples.

A Synthesis of Tin Salt of Aliphatic Monocarboxylic Acid

Preparation Example 1.1

First, 110 g (0.95 moles) of caproic acid as an aliphatic monocarboxylic acid was placed in a four-necked flask provided with a stirrer, a condenser, a thermometer and a nitrogen inlet tube. Then, 190 g (0.95 moles) of a 20% sodium hydroxide aqueous solution as an alkali aqueous solution was added gradually thereto, and the mixture was stirred under a nitrogen stream at 25° C. for 30 minutes. Further, a 50% aqueous solution containing 105 g (0.46 moles) of stannous chloride dihydrate as an inorganic tin compound was added thereto, and stirred for 30 minutes. The reaction mixture was allowed to stand for 5 minutes so that the layers were separated. The upper water layer was removed by decantation, and while increasing the temperature to 50° C., the lower layer was washed with water 5 times, and then dried so that tin caproate (tin salt I of aliphatic monocarboxylic acid) was obtained. This compound was confirmed to be tin caproate by infrared absorption spectroscopy.

Preparation Examples 1.2 to 1.6

According to Preparation Example 1.1, an alkali aqueous solution containing alkali was added to an aliphatic monocarboxylic acid shown in Table 1 in such an amount that the mole ratio was 1:1, and the mixture was stirred. Thus, a tin salt of aliphatic monocarboxylic acid as shown in Table 1 was formed. Then, the operation as in Preparation Example 1.1 was repeated, using an inorganic tin compound shown in Table 1, at a mole ratio and reaction conditions as shown in Table 1. Thus, tin salts II to VI of aliphatic monocarboxylic acid were obtained. In Preparation Example 1.3, a precipitate was formed by a reaction with the inorganic tin compound, and this was removed by filtration.

Preparation Example 1.7

Referring to Japanese Laid-Open Patent Publication No. 6-15170, a tin salt of aliphatic monocarboxylic acid was synthesized by the following method. First, 25 g of stannous oxide was refluxed together with 100 g of glacial acetic acid for 8 hours under a nitrogen stream, and the mixture was cooled to room temperature and then filtered. The filtrate was evaporated using a rotary evaporator, and then the resultant white solid was further vacuum-dried so that stannous acetate (tin salt VII of aliphatic monocarboxylic acid) was obtained. This compound was confirmed to be stannous acetate by infrared absorption spectroscopy.

Preparation Examples 1.8 and 1.9

According to the process of Preparation Example 1.7, the operation was performed using an aliphatic monocarboxylic acid and an inorganic tin compound shown in Table 1 at a ratio and reaction conditions as shown in Table 1, and thus tin salts VIII and IX of aliphatic monocarboxylic acid were obtained.

TABLE 1

| | Tin salt of aliphatic monocarboxylic acid | Aliphatic monocarboxylic acid or its salt | Inorganic tin compound | Synthesis method | Molar ratio[a] | Reaction temp. (° C.) | Melting point before treatment (° C.) | Notes |
|---|---|---|---|---|---|---|---|---|
| Preparation Ex. 1.1 | I | Sodium capronate | Stannous chloride | Double decomposition method | 2.05/1 | 25 | 70 | — |
| Preparation Ex. 1.2 | II | Ammonium butyrate | Stannous chloride | Double decomposition method | 2.1/1 | 25 | 67 | — |
| Preparation Ex. 1.3 | III | Capric acid diethanolamine salt | Stannous bromide | Double decomposition method | 2.3/1 | 50 | 73 | Filtration required |
| Preparation Ex. 1.4 | IV | Potassium myristate | Stannous chloride | Double decomposition method | 2.05/1 | 50 | 89 | — |
| Preparation Ex. 1.5 | V | Potassuim behenate | Stannous chloride | Double decomposition method | 2.05/1 | 60 | 104 | — |

TABLE 1-continued

| | Tin salt of aliphatic monocarboxylic acid | Aliphatic monocarboxylic acid or its salt | Inorganic tin compound | Synthesis method | Molar ratio[a] | Reaction temp. (° C.) | Melting point before treatment (° C.) | Notes |
|---|---|---|---|---|---|---|---|---|
| Preparation Ex. 1.6 | VI | Sodium capronate | Stannous sulfate | Double decomposition method | 1.9/1 | 50 | 70 | Filtration required |
| Preparation Ex. 1.7 | VII | Acetic acid | Stannous oxide | Direct method | 13.2/1 | 110 | 188 | Filtration required |
| Preparation Ex. 1.8 | VIII | Caproic acid | Stannous chloride | Direct method | 5.0/1 | 160 | 70 | Filtration required |
| Preparation Ex. 1.9 | IX | Butyric acid | Stannous oxide | Direct method | 6.1/1 | 160 | 67 | Filtration required |

[a] Molar ratio of aliphatic monocarboxylic acid or the salt thereof/inorganic tin compound

B. Preparation of Low Melting Point Tin Salt of Aliphatic Monocarboxylic Acid

Example 1.1

The tin salt I of aliphatic monocarboxylic acid obtained in Preparation Example 1.1 was heated and melted, and oxygen gas, which is an oxygen supplying substance, was bubbled into the molten tin salt at 75° C. for a contact treatment with oxygen. As a result, a low melting point tin salt of aliphatic monocarboxylic acid was obtained. Table 2 shows the name of the tin salt of aliphatic monocarboxylic acid and the oxygen supplying substance used; the reaction conditions; the weight increase ratio (%; based on the weight of tin atom); and the melting point and the appearance at ordinary temperature (30° C.) of the resultant compound. Table 2 also shows those of Examples 1.2 to 1.8 and Comparative Examples 1.1 to 1.3, which are described later.

Examples 1.2 to 1.8

Each of the tin salts of aliphatic monocarboxylic acid shown in Table 2 that were obtained in the preparation examples was brought in contact with an oxygen supplying substance under the conditions shown in Table 2. In Examples 1.2 and 1.7, a 30% hydrogen peroxide aqueous solution was dropped in the tin salt of aliphatic monocarboxylic acid and the mixture was stirred for a predetermined period. In Example 1.5, the tin salt of aliphatic monocarboxylic acid was allowed to stand in an ozone atmosphere for a predetermined period. In Example 1.6, when the tin caproate obtained in Preparation Example 1.6 was heated to a temperature higher than its melting point to be melted, opaqueness due to decomposition products derived from unreacted stannous sulfate was observed, and therefore these impurities were removed by filtration, and the filtrate was used in the subsequent operation.

As a result of the above-described operation, a low melting point tin salt of aliphatic monocarboxylic add was obtained in each example.

Comparative Examples 1.1 to 1.3

The tin salts of aliphatic monocarboxylic acid shown in Table 2 that were obtained in the preparation examples were heated and melted. In Comparative Example 1.1, the tin salt of aliphatic monocarboxylic acid was allowed to stand in a nitrogen atmosphere at 75° C. for 12 hours for a contact treatment. In Comparative Example 1.2, nitrogen was bubbled into the molten tin salt at 70° C. for 20 hours for a contact treatment. In Comparative Example 1.3, the tin salt of aliphatic monocarboxylic acid was allowed to stand in an oxygen atmosphere at 25° C. for 20 days for a contact treatment. The melting point of the tin salt of aliphatic monocarboxylic acid after the contact treatment was the same as the melting point of the tin salt before the treatment, and in none of the comparative examples, a low melting point tin salt of aliphatic monocarboxylic acid was obtained.

TABLE 2

| | Tin salt of aliphatic monocarboxylic acid (carbon number) | Oxygen supplying substance | Treatment method | Treatment temp. (° C.) | Treatment time | Weight increase ratio (%) | Melting point after treatment (° C.)[a] | Appearance after treatment[b] |
|---|---|---|---|---|---|---|---|---|
| Example 1.1 | I (6) | Oxygen | Bubbling | 75 | 12 hrs. | 13 | −9 | Liquid |
| Example 1.2 | II (4) | Hydrogen peroxide solution | Dropping | 25 | 0.5 hrs. | 13 | −18 | Liquid |
| Example 1.3 | IV (14) | Air | Bubbling | 90 | 20 hrs. | 10 | 51 | Solid |
| Example 1.4 | V (22) | Air | Bubbling | 130 | 30 hrs. | 10 | 77 | Solid |
| Example 1.5 | VI (6) | Ozone | Exposure | 50 | 6 hrs. | 13 | −9 | Liquid |
| Example 1.6 | IX (4) | Oxygen | Bubbling | 70 | 12 hrs. | 13 | −18 | Liquid |
| Example 1.7 | VIII (6) | Hydrogen peroxide solution | Dropping | 25 | 0.5 hrs. | 13 | −9 | Liquid |
| Example 1.8 | III (10) | Oxygen | Bubbling | 75 | 1 hr | 2 | 29 | Liquid |
| Com. Ex. 1.1 | III (10) | —[c] | Exposure | 75 | 12 hrs. | 0 | 73 | Solid |
| Com. Ex. 1.2 | II (4) | —[c] | Bubbling | 70 | 20 hrs. | 0 | 67 | Solid |
| Com. Ex. 1.3 | VII (2) | Oxygen | Exposure | 25 | 20 days | 0 | 188 | Solid |

[a] Melting point of aliphatic monocarboxylic acid after contact treatment (° C.)
[b] Appearance of aliphatic monocarboxylic acid after contact treatment
[c] Nitrogen As can be seen from Table 2, in Examples 1.1 to 1.8, low melting point tin salts of aliphatic monocarboxylic acid having melting points 20° C. lower than those before the contact with the oxygen supplying substance were obtained. In particular, when a tin salt of aliphatic monocarboxylic acid having 4 to 10 carbon atoms was used, and the weight increase ratio (in terms of the weight of tin) by the oxygen contact treatment was 1% or more, then all of the tin salts of aliphatic monocarboxylic acid were liquid at 30° C.

In Comparative Examples 1.1 to 1.3, the tin salts of aliphatic monocarboxylic acid after the treatment were solid. The melting points thereof were the same as those before the treatment, and not changed. In Comparative Examples 1.1 and 1.2, a contact with oxygen was prevented, so that the weight was not increased. Also in Comparative Example 1.3, there was no change in the weight.

Figure 2:
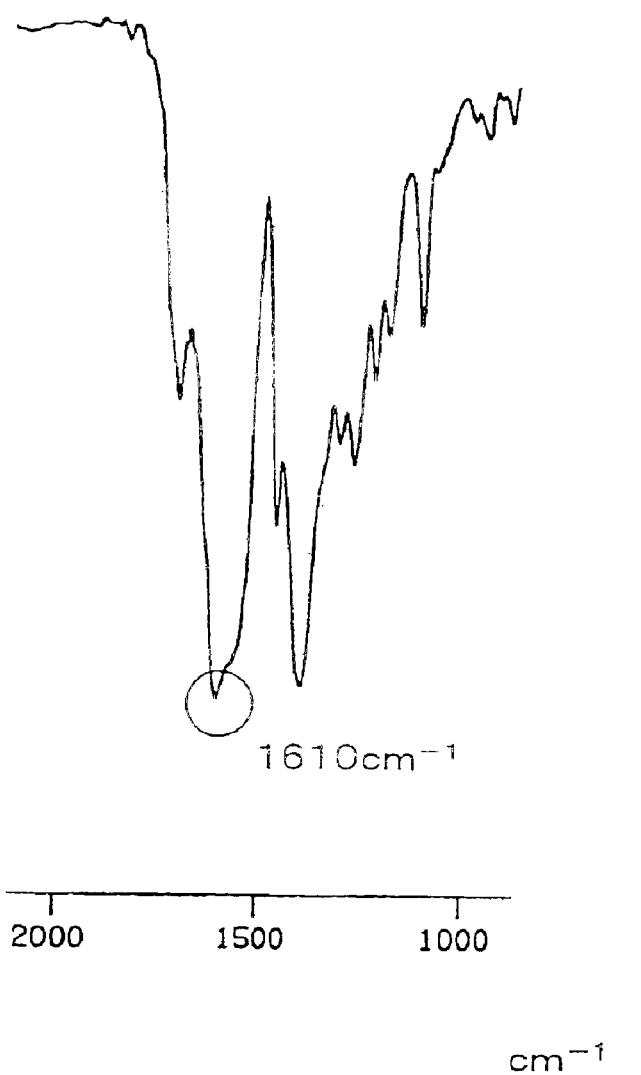
FIG. 2 is a chart showing an infrared absorption spectrum of a low melting point tin caproate (after an oxygen contact treatment) obtained in Example 1.1.

The infrared absorption spectra of the tin salts I to VI and VII to IX of aliphatic monocarboxylic acid before the contact treatment with the oxygen supplying substance that were obtained in the above preparation examples were obtained. As a result, all of the tin salts of aliphatic monocarboxylic acid were confirmed to have a strong peak derived from the C=O double bond in the vicinity of 1550 cm$^{-1}$. On the other hand, the low melting point tin salts of aliphatic monocarboxylic acid obtained in Examples 1.1 to 1.8 exhibited a strong peak derived from the C=O double bond in the vicinity of 1610 cm$^{-1}$. FIG. 1 shows the infrared absorption spectrum of the tin caproate (tin salt I of aliphatic monocarboxylic acid) obtained in Preparation Example 1.1. FIG. 2 shows the infrared absorption spectrum of the low melting point tin caproate obtained in Example 1.1.

Example 2.1

First, 0.95 moles of n-heptanoic acid as aliphatic monocarboxylic acid was placed in a four-necked flask provided with a stirrer, a condenser, a thermometer and a nitrogen inlet tube. Then, a 20% aqueous solution of sodium hydroxide (0.95 moles) as an alkali aqueous solution was added gradually thereto, and the mixture was stirred under a nitrogen stream at 25° C. for 30 minutes. Further, a 50% aqueous solution containing 0.46 moles of stannous chloride dihydrate as an inorganic tin compound was added in the entire amount thereto, and stirred for 30 minutes. The mixture was allowed to stand for 5 minutes so that the layers were separated. The upper water layer was removed by decantation, and while increasing the temperature to 50° C., the lower layer was washed with water 5 times, and then dried so that stannous n-heptanoate was obtained as a tin salt of aliphatic monocarboxylic acid. This compound was confirmed to be stannous n-heptanoate by infrared absorption spectroscopy. A 30% hydrogen peroxide aqueous solution was dropped in the obtained stannous n-heptanoate at 25° C. and stirred for 0.5 hours for an oxygen contact treatment. As a result, a liquid stannous n-heptanoate (product i) was obtained. Table 3 shows the tin salt of aliphatic monocarboxylic acid and the oxygen supplying substance that were employed and the weight increase ratio (%; based on the weight of the tin atom), the melting point and the appearance at 30° C. of the resultant compound. Table 3 also shows those of Examples 2.2 to 2.5 and Comparative Examples 2.1 to 2.3, which are described later.

Examples 2.2 to 2.5

Tin salts of aliphatic monocarboxylic add shown in Table 3 were prepared by the method shown in Table 3 (double decomposition method or direct method). They were brought in contact with the oxygen supplying substance shown in Table 3 for an oxygen contact treatment. In Examples 2.2, 2.4 and 2.5, the tin salt of aliphatic monocarboxylic acid was heated and melted. Then, oxygen gas in Example 2.2 and air in Example 2.5 were bubbled into the molten tin salt at 75° C. for 12 hours, and in Example 2.4, oxygen was bubbled into the molten tin salt at 75° C. for one hour for a contact treatment with oxygen. In Example 2.3, the tin salt of aliphatic monocarboxylic acid was allowed to stand in an ozone atmosphere for 6 hours for a contact treatment with oxygen. As a result, low melting point tin salts of aliphatic monocarboxylic acid (products ii to v) were obtained.

Comparative Example 2.1

Stannous caproate (product vi) was obtained from caproic acid and an inorganic tin compound by the double decomposition method. With this, no oxygen contact treatment was performed.

Comparative Examples 2.2 and 2.3

A tin salt of aliphatic monocarboxylic add shown in Table 3 was heated and melted. In Comparative Example 2.2, nitrogen was bubbled into the molten tin salt at 750° C. for 20 hours. In Comparative Example 2.3, the tin salt of aliphatic monocarboxylic acid was allowed to stand in an oxygen atmosphere at 25° C. for 20 days for a contact treatment. As a result, products vii and viii were obtained.

TABLE 3

| | Tin salt of aliphatic monocarboxylic acid | Preparation method[a] | Oxygen supplying substance | Product[b] | Weight increase ratio (%) | Melting point (° C.) | Appearance |
|---|---|---|---|---|---|---|---|
| Example 2.1 | Stannous n-heptanoate | Double decomposition method | Hydrogen peroxide solution | i | 13 | −11 | Liquid |
| Example 2.2 | Stannous caproate | Double decomposition method | Oxygen | ii | 13 | −9 | Liquid |
| Example 2.3 | Stannous n-heptanoate | Double decomposition method | Ozone | iii | 13 | −11 | Liquid |
| Example 2.4 | Stannous n-decanoate | Direct method | Oxygen | iv | 2 | 29 | Liquid |

TABLE 3-continued

|  | Tin salt of aliphatic monocarboxylic acid | Preparation method[a] | Oxygen supplying substance | Product[b] | Weight increase ratio (%) | Melting point (° C.) | Appearance |
|---|---|---|---|---|---|---|---|
| Example 2.5 | Stannous butyrate | Double decomposition method | Air | v | 10 | −18 | Liquid |
| Com. Ex. 2.1 | Stannous caproate | Double decomposition method | None | vi | — | 70 | Solid |
| Com. Ex. 2.2 | Stannous n-heptanoate | Direct method | —[c] | vii | 0 | 66 | Solid |
| Com. Ex. 2.3 | Stannous acetate | Direct method | Oxygen | viii | 0 | 188 | Solid |

[a]Method for preparing tin salt of aliphatic monocarboxylic acid
[b]Tin salt of linear aliphatic monocarboxylic acid obtained by treatment
[c]Nitrogen As can be seen from Table 3, in all of the products i to v obtained by an oxygen contact treatment, the weight increase ratio based on the tin weight was 2% or more. Furthermore, the melting point was reduced compared with the compounds before the treatment, and the appearance thereof was changed from solid to liquid. For example, in Example 2.2 in which the oxygen contact treatment was performed, the weight was increased compared with Comparative Example 2.1 in which no oxygen contact treatment was performed, and the appearance was changed from solid to liquid. When the compound was brought in contact with nitrogen instead of oxygen as in Comparative Example 2.2, the weight did not increase, the melting point was not changed, and the compound stayed a solid. On the other hand, in Example 2.3 in which the tin monocarboxylate was subjected to an oxygen contact treatment, the weight was increased, the melting point was reduced, and the appearance was changed to liquid.

In Comparative Example 2.3 in which tin acetate was used, the weight was not increased, the melting point was not changed, and the compound stayed solid.

B. Solubility of the Low Melting Point Tin Salt of Aliphatic Monocarboxylic Acid in a Solvent Examples 3.1 to 3.5

Each of the low melting point tin salts of aliphatic monocarboxylic acid (products i to v) obtained in Examples 2.1 to 2.5 was dissolved in a solvent as shown in Table 4 in a concentration (described under each solvent name) as shown in Table 4. The state of the solution after being allowed to stand at 30° C. for one hour was visually observed. The results of these tests are shown in Table 4. In Table 4, cases where the solution was visually confirmed to be clear are marked by ○, and cases where the solution was opaque are marked by X.

Comparative Example 3.1 to 3.3

The products vi to viii obtained in Comparative Examples 2.1 to 2.3 were subjected to the same tests as in Examples 3.1 to 3.5. Table 4 shows the results.

TABLE 4

|  | Treated product[a] | Toluene | | | Ethanol | Hexane | Chloroform | Acetone | Diethyl ether | Dimethyl-formamide | Ethyl acetate | Acetic acid | Aqueous acetic acid[b] | Toluene-ethanol mixed solvent[c] |
|---|---|---|---|---|---|---|---|---|---|---|---|---|---|---|
|  |  | 10% | 30% | 50% | 30% | 30% | 30% | 30% | 30% | 30% | 30% | 30% | 30% | 30% |
| Example 3.1 | i | ○ | ○ | ○ | ○ | ○ | ○ | ○ | ○ | ○ | ○ | ○ | ○ | ○ |
| Example 3.2 | ii | ○ | ○ | ○ | ○ | ○ | ○ | ○ | ○ | ○ | ○ | ○ | ○ | ○ |
| Example 3.3 | iii | ○ | ○ | ○ | ○ | ○ | ○ | ○ | ○ | ○ | ○ | ○ | ○ | ○ |
| Example 3.4 | iv | ○ | ○ | ○ | ○ | ○ | ○ | ○ | ○ | ○ | ○ | ○ | ○ | ○ |
| Example 3.5 | v | ○ | ○ | ○ | ○ | ○ | ○ | ○ | ○ | ○ | ○ | ○ | ○ | ○ |
| Com. Ex. 3.1 | vi | X | X | X | X | X | X | X | X | X | X | X | X | X |
| Com. Ex. 3.2 | vii | X | X | X | X | X | X | X | X | X | X | X | X | X |
| Com. Ex. 3.3 | viii | X | X | X | X | X | X | X | X | X | X | X | X | X |

[a]Tin salt of aliphatic monocarboxylic acid obtained by treatment
[b]Acetic acid:Water = 9:1 (weight ratio)
[c]Toluene:Ethanol = 3:1 (weight ratio)

As can be seen from Table 4, all of the low melting point tin monocarboxylates that were obtained by a sufficient oxygen contact treatment and that were liquid at 30° C. (Examples 3.1 to 3.5; products i to v) were soluble in various solvents in a wide range from non-polar solvents to polar solvents. Each of the solutions remained clear after one hour had passed.

On the other hand, none of the tin monocarboxylates that had not been subjected to the oxygen contact treatment (Comparative Examples 3.1 and 3.2; products vi to vii) were dissolved in any of the solvents and the resultant mixtures were opaque and opaque substances were deposited after one hour. Also, stannous acetate that had been subjected to the oxygen contact treatment (Comparative Example 3.3; product viii) was not dissolved in any of the solvents, and the resultant mixture was opaque and opaque substances were deposited after one hour.

C. Preparation of Tin Oxide Film

Example 4.1

The low melting point tin monocarboxylate obtained in Example 2.1 was diluted in a solvent shown in Table 5 so that a coating liquid was obtained. This was applied onto a glass substrate using a spin coater, and then dried. Then, the substrate was heated to increase the temperature to 500° C. at a temperature-increase ratio of 10° C. per min, and baking was performed at 500° C. for one hour. Thus, a tin oxide film was formed.

The state of the coating film obtained by application of the coating liquid onto the substrate was visually observed. Furthermore, the thickness of the film obtained by baking was measured, and the state of the surface (regarding cracks and transparency) thereof was visually observed. Table 5 shows the results. In the section "state of coating film" in Table 5, cases where the coating film was uniform and smooth are marked by ○, cases where it was non-uniform are marked by Δ, and cases where it was non-uniform and opaque are marked by X. The thickness of the film was measured with a stylus type film thickness measuring device DEKTAC 3ST manufactured by ULVAC Inc. In the section "transparency" in Table 5, cases where the film was visually confirmed to be uniform, smooth and transparent are marked by ○, and cases where it was non-uniform and opaque are marked by X. Table 5 also shows the results of Examples 4.2 to 4.7 and Comparative Examples 4.1 to 4.4 described later.

Examples 4.2 to 4.7

A coating liquid was prepared using either one of the low melting point tin monocarboxylates ii to v obtained in Examples 2.2 to 2.5 and a solvent shown in Table 5 and evaluated in the same manner as in Example 4.1.

Comparative Examples 4.1 to 4.4

A coating liquid was prepared using either one of the products vi to viii obtained in Comparative Examples 2.1 to 2.3 and stannous 2-ethyl hexanoate, and a solvent shown in Table 5 and evaluated in the same manner as in Example 4.1.

TABLE 5

| Coating liquid | Treated product[a] | Treated product[a] | Ethanol | Toluene | Acetone | Ethyl acetate | PGMEA[b] | Solubility[c] | State of coating film | Film thickness after baking (μm) | Cracks | Transparency |
|---|---|---|---|---|---|---|---|---|---|---|---|---|
| Example 4.1 | i | 30 | 70 | 0 | 0 | 0 | 0 | Sufficient | ○ | 0.42 | Absent | ○ |
| Example 4.2 | ii | 10 | 70 | 0 | 0 | 0 | 20 | Sufficient | ○ | 0.11 | Absent | ○ |
| Example 4.3 | ii | 90 | 10 | 0 | 0 | 0 | 0 | Sufficient | ○ | 0.8 | Absent | ○ |
| Example 4.4 | iii | 90 | 0 | 0 | 0 | 10 | 0 | Sufficient | ○ | 0.6 | Absent | ○ |
| Example 4.5 | iii | 30 | 0 | 0 | 70 | 0 | 0 | Sufficient | ○ | 0.13 | Absent | ○ |
| Example 4.6 | iv | 30 | 15 | 55 | 0 | 0 | 0 | Sufficient | ○ | 0.23 | Absent | ○ |
| Example 4.7 | v | 10 | 80 | 10 | 0 | 0 | 0 | Sufficient | ○ | 0.17 | Absent | ○ |
| Com. Ex. 4.1 | vi | 30 | 70 | 0 | 0 | 0 | 0 | Insufficient | X | —[d] | Many cracks present | X |
| Com. Ex. 4.2 | vii | 30 | 50 | 0 | 20 | 0 | 0 | Insufficient | X | —[d] | Many cracks present | X |
| Com. Ex. 4.3 | viii | 30 | 10 | 0 | 0 | 60 | 0 | Insufficient | X | —[d] | Many cracks present | X |
| Com. Ex. 4.4 | Stannous 2-ethyl-hexanoate | 20 | 80 | 0 | 0 | 0 | 0 | Sufficient | Δ | 0.27 | Many cracks present | X |

[a] Tin salt of aliphatic monocarboxylic acid obtained by treatment
[b] Propylene glycol monomethyl ether acetate
[c] Solubility of tin salt in solvent
[d] Film thickness could not be measured As can be seen from Table 5, when a liquid low melting point tin monocarboxylate was used (Examples 4.1 to 4.7; products i to v), a clear coating liquid was obtained, and a transparent tin oxide film without cracks was obtained by baking a substrate having a coating film derived from the coating film. On the other hand, when the tin monocarboxylate whose melting point was not low was used (Comparative Examples 4.1 to 4.3; products vi to viii), no transparent coating liquid could be obtained. When a substrate having a coating film derived from such a coating liquid was formed was baked, the obtained film had a large number of cracks or the film was peeled off from the substrate. Even though the film was not peeled off, the film was not transparent. In Comparative Example 4.4, stannous 2-ethylhexanoate could be dissolved in ethanol. However, when baking was performed after a coating film was formed onto a glass substrate, the resultant oxide film shrank, so that a large number of cracks occurred, or the film was peeled off from the substrate. In addition, the transparency of the resultant film that was not detached was insufficient.

D. Preparation of ITO Film

Examples 5.1 to 5.7

Each of the tin salt of carboxylic acid and indium compounds shown in Table 6 was dissolved in a solvent (single solvent or mixed solvent) shown in Table 6 at a ratio (wt %) shown in Table 6 so that a coating liquid for preparing an ITO film was obtained. The tin monocarboxylate used was either one of the products i to v obtained in Examples 2.1 to 2.5. The indium caproate used in Example 5.5 was prepared by the double decomposition method by reacting 3 moles of sodium n-caproate with 1 mol of indium chloride. Other indium compounds were commercially available products.

The state of the coating liquid at the time when the coating liquid was prepared was visually observed. The results thereof are shown in the section "state of coating liquid" in Table 6. Cases where the coating liquid was clear and free from settlement or the like are marked by ○, and cases where there were settlements or turbidity are marked by X.

Then, the obtained coating liquid was applied onto a glass substrate using a spin coater, and was subjected to pre-baking at a temperature of 50 to 60° C. for drying. The state of the film after the pre-baking was visually observed. The results thereof are shown in the section "film after pre-baking" in Table 6. Cases where the film was very transparent and had no aggregation or non-uniformity are marked by ○, cases where the coating film was uniform and had no aggregation but the clarity was slightly poor are marked by Δ, and cases where the coating film had significant aggregation, non-uniformity and opaqueness are marked by X.

Then, the glass substrate after the pre-baking was heated to 550° C. and subjected to the baking at 550° C. for 2 hours, so that an ITO film was obtained. The uniformity and the smoothness of the film that was obtained as a final product by the baking were visually observed. The results thereof are shown in the section "film after baking" in Table 6. Cases where the film was uniform and very smooth are marked by ⊚, cases where the film was uniform and smooth are marked by ○, cases where the smoothness and the uniformity of the film were slightly poor are marked by Δ, and cases where the smoothness was not sufficient and there was much non-uniformity are marked by X. Furthermore, presence or absence of cracks in the film after the baking was visually observed. The results are shown in the section "cracks" in Table 6. Regarding the transparency of the resultant film, cases where the film was very transparent are marked by ⊚, cases where the film was sufficiently transparent are marked by ○, cases where there was turbidity or haze are marked by X. The results are shown in the section "transparency of film" in Table 6.

Comparative Examples 5.1 to 5.3

Each of the tin carboxylate and indium compounds shown in Table 6 was dissolved in a solvent (single solvent or mixed solvent) shown in Table 6 at a ratio (wt %) shown in Table 6 so that a coating liquid for preparing an ITO film was obtained. The tin monocarboxylate used was the product vi obtained in Comparative Example 2.1 for Comparative Example 5.1 and the product vii obtained in Comparative Example 2.2 for Comparative Example 5.2. In Comparative Example 5.3, a commercially available stannous 2-ethyl hexanoate was used.

Using the obtained coating liquids, ITO films were prepared in the same manner as in Examples 5.1 to 5.7 and evaluated in the same manner. Table 6 shows the results.

TABLE 6

|  | Tin salt of aliphatic monocarboxylic acid | | Indium | | Solvent | | State of coating liquid | Film after pre-baking[a] | Film after baking[b] | Cracks | Transparency of film[c] |
|---|---|---|---|---|---|---|---|---|---|---|---|
|  | Product or compound | wt % | Compound | wt % | Compound | wt % |  |  |  |  |  |
| Example 5.1 | i | 79 | Indium chloride | 1 | Ethanol | 20 | ○ | Δ | ○ | Absent | ○ |
| Example 5.2 | ii | 4 | Indium nitrate | 16 | Acetylacetone | 80 | ○ | Δ | ○ | Absent | ○ |
| Example 5.3 | ii | 20 | Acetylacetone indium salt | 20 | Acetone PGMEA[d] | 50 10 | ○ | Δ | ○ | Absent | ○ |
| Example 5.4 | iii | 1 | Indium acetate | 9 | Toluene Acetylacetone | 70 20 | ○ | Δ | ○ | Absent | ○ |
| Example 5.5 | iii | 0.5 | Indium capronate | 9.5 | Hexane Ethanol | 72 18 | ○ | ○ | ⊚ | Absent | ⊚ |
| Example 5.6 | iv | 79 | Indium 2-ethyl-hexanoate | 1 | Tetrahydrofuran | 20 | ○ | ○ | ○ | Absent | ⊚ |
| Example 5.7 | v | 0.5 | Indium neodecanoate | 9.5 | Hexane | 90 | ○ | Δ | Δ | Absent | ○ |
| Com. Ex. 5.1 | vi | 10 | Indium chloride | 10 | Ethanol | 80 | X | X | X | Many cracks present | X |
| Com. Ex. 5.2 | vii | 10 | Indium nitrate | 10 | Acetylacetone | 80 | X | X | X | Many cracks present | X |
| Com. Ex. 5.3 | Stannous 2-ethyl-hexanoate | 79 | Indium 2-ethyl-hexanoate | 1 | Hexane Ethanol | 72 18 | ○ | ○ | Δ | Many cracks present | X |

[a] State of film after pre-baking
[b] Uniformity and smoothness of film after baking
[c] Transparency of film after baking
[d] Propylene glycol monomethyl ether acetate As can be seen from Table 6, each of the coating liquids containing a liquid low melting point tin salt of aliphatic monocarboxylic acid (each of the products i to v) and an indium compound was transparent, and an ITO film prepared by using the coating liquid was uniform, free from cracks and transparent (Examples 5.1 to 5.7). When the indium salt of monocarboxylic acid having 5 to 8 carbon atoms was used as an indium compound, ITO films having very high transparency can be obtained (Examples 5.5 and 5.6). When the monocarboxylic acid constituting the indium monocarboxylate was linear (Example 5.5), a very good film further having excellent uniformity and smoothness was obtained.

On the other hand, when a coating liquid was prepared, using a solid tin monocarboxylate and an indium compounds (Comparative Examples 5.1 and 5.2), no transparent coating liquid was obtained, and when a substrate on which a coating film was formed was baked, the resultant film was not uniform and had a large number of cracks or the film was peeled off from the substrate.

In Comparative Example 5.3, stannous 2-ethyl hexanoate was soluble in a mixed solution of hexane and ethanol and a transparent coating liquid was obtained. However, the film obtained by baking was not sufficiently uniform and was opaque.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A low melting point tin salt of aliphatic monocarboxylic acid obtained by a process comprising,
    reacting an aliphatic monocarboxylic acid having 4 to 30 carbon atoms or its salt and an inorganic tin compound so as to prepare a tin salt of aliphatic monocarboxylic acid; and
    bringing the tin salt in contact with an oxygen supplying substance.

2. The low melting point tin salt of claim 1, wherein the aliphatic monocarboxylic acid has 4 to 22 carbon atoms.

3. The low melting point tin salt of claim 2, wherein the aliphatic monocarboxylic acid is a linear aliphatic monocarboxylic acid having 4 to 10 carbon atoms.

4. A method for producing a low melting point tin salt of aliphatic monocarboxylic acid, comprising:
    reacting an aliphatic monocarboxylic acid having 4 to 30 carbon atoms or its salt and an inorganic tin compound so as to prepare a tin salt of aliphatic monocarboxylic acid; and
    bringing the tin salt in contact with an oxygen supplying substance.

5. The method of claim 4, wherein the oxygen supplying substance is oxygen or a gas containing oxygen.

6. The method of claim 4, wherein the tin salt of aliphatic monocarboxylic acid is brought in contact with the oxygen supplying substance at a temperature that is equal to or higher than the melting point of the tin salt of aliphatic monocarboxylic acid before the contact.

7. A coating liquid for forming a metal oxide film, wherein the coating liquid comprises a low melting point tin salt of aliphatic monocarboxylic acid of claim 1 and a solvent.

8. The coating liquid of claim 7, wherein the low melting point tin salt is derived from a linear aliphatic monocarboxylic acid having 4 to 10 carbon atoms.

9. The coating liquid of claim 7, wherein a 30 wt % ethanol solution of the low melting point tin salt of aliphatic monocarboxylic acid is clear when the solution is allowed to stand at 30° C. for one hour.

10. The coating of claim 7, further comprising an indium compound.

11. The coating liquid of claim 10, wherein the total amount of the low melting point tin salt of aliphatic monocarboxylic acid and the indium compound is 1 to 95 wt % in the coating liquid.

12. The coating liquid of claim 7, wherein the solvent is at least one selected from the group consisting of hydrocarbon solvents, alcohol solvents, ester solvents, ether solvents, and ketone solvents.

13. The method of claim 5, wherein the tin salt of aliphatic monocarboxylic acid is brought in contact with the oxygen supplying substance at a temperature that is equal to or higher than the melting point of the tin salt of aliphatic monocarboxylic acid before the contact.

14. The coating liquid of claim 8, wherein a 30 wt % ethanol solution of the low melting point tin salt of aliphatic monocarboxylic acid is clear when the solution is allowed to stand at 30° C. for one hour.

15. The coating of claim 8, further comprising an indium compound.

16. The coating of claim 9, further comprising an indium compound.

17. The coating liquid of claim 10, wherein the solvent is at least one selected from the group consisting of hydrocarbon solvents, alcohol solvents, ester solvents, ether solvents, and ketone solvents.

* * * * *